United States Patent
Murata et al.

(10) Patent No.: US 9,339,218 B2
(45) Date of Patent: May 17, 2016

(54) CONCENTRATION MEASURING DEVICE

(71) Applicant: HORIBA, Ltd., Kyoto-shi, Kyoto (JP)

(72) Inventors: Tomoyuki Murata, Kyoto (JP); Takao Minai, Kyoto (JP); Takaaki Yada, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 14/329,836

(22) Filed: Jul. 11, 2014

(65) Prior Publication Data
US 2015/0014161 A1    Jan. 15, 2015

(30) Foreign Application Priority Data

Jul. 12, 2013    (JP) .................................. 2013-146959

(51) Int. Cl.
*G01N 33/48* (2006.01)
*A61B 5/145* (2006.01)
(Continued)

(52) U.S. Cl.
CPC ........... *A61B 5/14532* (2013.01); *A61B 5/1486* (2013.01); *B01L 3/5023* (2013.01); *C12Q 1/001* (2013.01); *G01N 33/66* (2013.01); *B01L 2300/045* (2013.01); *B01L 2300/0645* (2013.01); *B01L 2300/0654* (2013.01); *B01L 2300/0681* (2013.01); *B01L 2300/0816* (2013.01); *B01L 2300/0887* (2013.01); *G01N 27/3273* (2013.01); *G01N 2021/035* (2013.01)

(58) Field of Classification Search
CPC .......... G01N 33/5302; G01N 21/6428; G01N 15/1484; G01N 2015/1486; G01N 2021/6441; G01N 33/50; G01N 2015/0073; G01N 21/274; G01N 21/6486; G01N 21/8483; G01N 2800/52; G01N 33/49; G01N 33/526
See application file for complete search history.

(56) References Cited

U.S. PATENT DOCUMENTS 5,179,288 A * 1/1993 Miffitt et al. ................... 250/564
8,467,055 B2 * 6/2013 Imanishi et al. ............... 356/344
(Continued)

FOREIGN PATENT DOCUMENTS

JP             434354 A     2/1992
JP           4230840 A      8/1992
(Continued)

OTHER PUBLICATIONS

European Patent Office, Extended European Search Report Issued in Application No. 14176536.2, Nov. 27, 2014, Germany, 7 pages.

*Primary Examiner* — Michael P Stafira
(74) *Attorney, Agent, or Firm* — Alleman Hall McCoy Russell & Tuttle LLP (57) ABSTRACT

A concentration measuring device having a spot-application region, and a configuration capable of measuring the concentration of an object component in the sample liquid dropped on the spot-application region, the concentration measuring device including: a light irradiation device, which is provided on a side below the spot-application region, for emitting an irradiation light having a wavelength absorbable by a coloring matter in the dropped sample liquid. The irradiation light passes through the spot-application region, thereby the sample liquid dropped on the spot-application region is irradiated with the irradiation light from the side below the spot-application region. As a result, a non-covered region in the spot-application region can be easily found by visual observation. The spot-application region is composed of, for example, a through hole formed on the supporting film and a separation membrane that blocks the through hole.

5 Claims, 8 Drawing Sheets

(51) Int. Cl.
  *A61B 5/1486* (2006.01)
  *B01L 3/00* (2006.01)
  *C12Q 1/00* (2006.01)
  *G01N 33/66* (2006.01)
  *G01N 27/327* (2006.01)
  *G01N 21/03* (2006.01)

(56) References Cited

U.S. PATENT DOCUMENTS

| | | | |
|---|---|---|---|
| 2002/0192833 A1* | 12/2002 | Pan et al. | 436/164 |
| 2003/0157724 A1* | 8/2003 | Petrich et al. | 436/164 |
| 2003/0160961 A1* | 8/2003 | Hafeman et al. | 356/433 |
| 2004/0162470 A1* | 8/2004 | Tu | 600/316 |
| 2008/0138852 A1* | 6/2008 | Winkelman et al. | 435/40.5 |
| 2008/0180658 A1* | 7/2008 | Samsoondar | 356/246 |
| 2011/0151502 A1* | 6/2011 | Kendall et al. | 435/39 |
| 2012/0064615 A1* | 3/2012 | Petrich et al. | 435/288.7 |
| 2013/0230879 A1* | 9/2013 | Neeves et al. | 435/29 |

FOREIGN PATENT DOCUMENTS

| | | |
|---|---|---|
| JP | 9119914 A | 5/1997 |
| JP | D1222931 S | 11/2004 |
| JP | 2006126046 A | 5/2006 |

\* cited by examiner

CONCENTRATION MEASURING DEVICE

FIELD OF THE INVENTION

The present invention relates to a concentration measuring device that measures the concentration of components such as grape sugar, uric acid, lactic acid, cholesterol and the like contained in sample liquids such as blood and the like. Particularly, the present invention relates to a concentration measuring device constituted to be able to measure concentration of the aforementioned components from one drop of a sample liquid dropped on a small region (region receiving a sample liquid) called a spot-application region (or a spot-applying part).

BACKGROUND OF THE INVENTION

A concentration measuring device is known, which is capable of measuring a concentration of a blood component such as grape sugar (glucose) and the like with an electrode type sensor based on the enzyme electrode method by supplying one drop of blood to a small region for receiving a sample liquid called a "spot-application region". The spot-application region is a target area for a user to drop a sample liquid to such as blood and the like, and also a receiving port of a sample liquid for a concentration measuring device.

In a conventionally known concentration measuring device (e.g., design registration No. 1222931 "liquid component concentration meter" and the like), generally, a case opening is formed on an upper surface of the body (case or housing) of a device, and a spot-application region for receiving a sample liquid is provided at the center in the case opening. The spot-application region is a small circular region having a diameter of about 3 mm-4 mm. One drop of the collected blood is dropped on the spot-application region (generally about 5-20 µL (microliter)), and a measurement starting switch is switched on, and then the concentration of the object component in the blood is measured by an electrode type sensor (also called enzyme electrode and the like) inside the device.

Figure 7A:
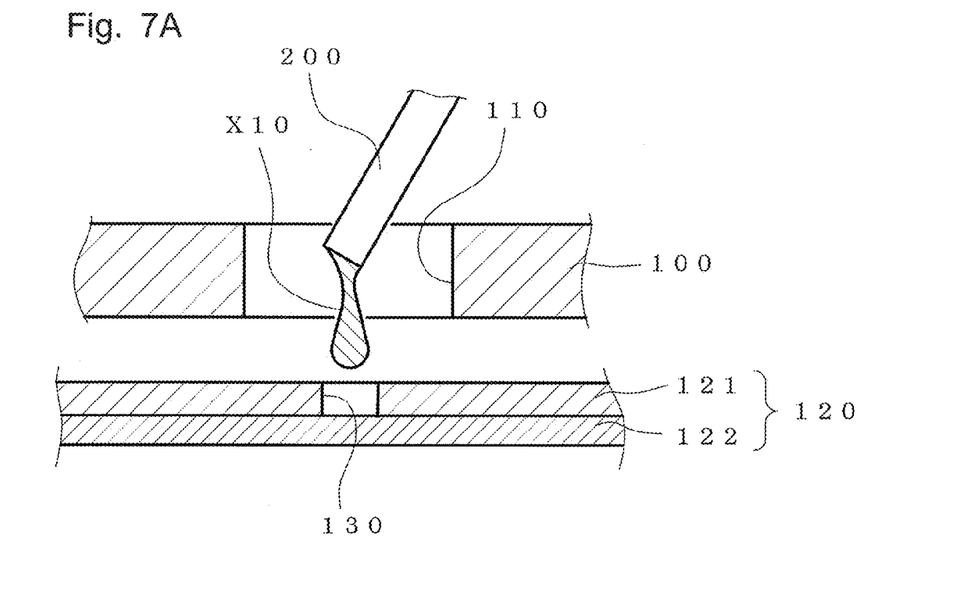
FIGS. 7A and 7B show a cross-section view (FIG. 7A) of a spot-application region of a conventional concentration measuring device with blood being dropped, and a cross-section view (FIG. 7B), showing measurement of a component concentration by an electrode type sensor.
Figure 7B:
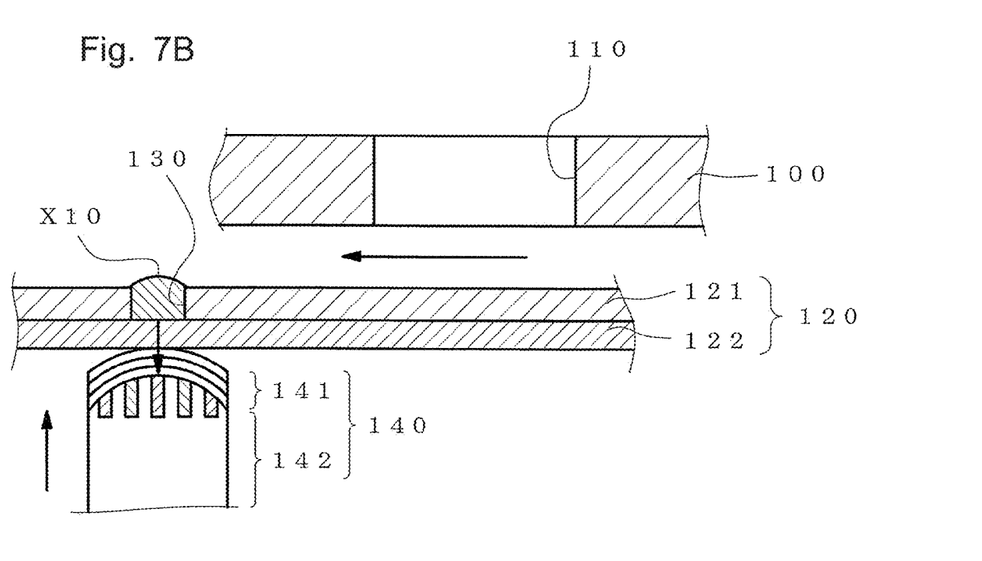

FIGS. 7A and 7B are cross-sectional views showing an example manner to measure, by an electrode type sensor, the concentration of the components in the blood dropped on the spot-application region of the above-mentioned concentration measuring device.

As shown in FIG. 7A, a case opening 110 is formed at a predetermined position of a case 100 of the concentration measuring device. A belt-shaped film 120 having spot-application regions at given intervals is set right beneath the case opening 110. When a user looks into the case opening from the outside, the main surface of the film is seen. In this constitution, the film 120 is intermittently fed from a delivery roll (not shown) to a winding roll (not shown) by a constant length such that a new spot-application region is positioned at the center in the case opening 110 for each measurement. The film 120 (whole film including delivery roll and winding roll) is provided as a replaceable cartridge.

The film 120 has a two-layer structure comprising a supporting film 121 as an upper layer and a blood cell separating membrane 122 as a lower layer. The blood cell separating membrane 122 is one kind of a filter membrane having many minute holes through which only the blood plasma can penetrate.

In the supporting film 121, through holes 130 having a diameter of about 3-4 mm to be the opening of the spot-application region are formed at a predetermined space in the longitudinal direction (feeding direction), and a blood cell separating membrane 122 is exposed on the bottom of each through hole. The through holes 130 and the blood cell separating membrane 122 on the inner bottom surface constitute the spot-application region. When blood is dropped in the through hole, the plasma in the blood penetrates the blood cell separating membrane and oozes out on the undersurface of the film.

As shown in FIG. 7A, sample blood X10 is dropped on the through hole 130 which is a spot-application region from an injection syringe, a micropipette 200 or the like, and when the measurement starting switch is switched on, the belt-shaped film 120 is horizontally fed by a predetermined length and stops as shown in FIG. 7B. Then, an electrode type sensor 140 ascends from below the through hole 130 and the top surface thereof (projected to form a spherical surface in preferable embodiment) comes into contact with the undersurface of the blood cell separating membrane 122 where the blood plasma has oozed out, whereby the top surface of the electrode type sensor 140 contacts the blood plasma. In FIGS. 7A and B, the magnitude correlation between the through hole and the electrode type sensor, and the ratio of layer thickness of respective layers are ignored and the structure is exaggeratingly depicted for the sake of explanation.

The outline of the principle of the concentration measurement by the above-mentioned electrode type sensor 140 is as follows in an example of the concentration measurement of blood glucose based on the hydrogen peroxide electrode method which is one kind of the enzyme electrode methods.

(A) Blood plasma that penetrated the blood cell separating membrane 121 contacts the top part of the electrode type sensor 140.

(B) grape sugar contained in the blood plasma passes through a cap film 141 formed as a surface layer of the electrode type sensor 140. The cap film 141 has a tree-layer structure (diffusion limiting film as surface layer, grape sugar oxidize immobilizing film as middle layer, hydrogen peroxide selective permeable film as under layer), and covers the upper surface of a hydrogen peroxide electrode 142 which is the main body of the sensor.

(C) When grape sugar passes through the cap film 141, it is decomposed by a catalytic action of an enzyme in the cap film middle layer to produce gluconic acid and hydrogen peroxide, and hydrogen peroxide penetrates a hydrogen peroxide selective permeable film of the cap film under layer to reach a hydrogen peroxide electrode. The hydrogen peroxide electrode 142 has a concentric cylinder-shaped structure, wherein a working electrode (anode, Pt) is provided in the central part. On the outer side thereof, a reference electrode (AgCl) is provided via an insulating layer. Then, on the outer side thereof, a counter electrode (cathode, Ag) is provided via an insulating layer.

The electrode type sensor (enzyme electrode) is explained in detail in, for example, JP-A-H4-34354 "ENZYME ELECTRODE", JP-A-H9-119914 "BIOSENSOR", JP-A-2006-126046 "WASHING TREATMENT METHOD OF ELECTRODE TYPE SENSOR, WASHING TREATMENT MECHANISM AND CONCENTRATION MEASURING INSTRUMENT EQUIPPED WITH THE MECHANISM" and the like. In addition, the mechanism for setting the above-mentioned film as a replaceable cartridge is explained in detail in, for example, JP-A-H4-230840 "CONCENTRATION MEASURING DEVICE" and the like.

In a concentration measuring device as mentioned above, for example, when grape sugar is the measurement target, it is recommended to use an aqueous grape sugar solution having a known concentration (standard concentration test solution) as a sample liquid for calibration and, for initial sensitivity adjustment and periodic sensitivity modification, drop the standard concentration test solution into a spot-application region, and adjust the indicated values on the concentration measuring device to be appropriate.

The concentration measuring device as mentioned above can measure the concentration of the object component by simply receiving a drop of a sample liquid from an injection syringe, a micropipette or the like.

However, the present inventors have detailedly studied the operability of a concentration measuring device as mentioned above, and found that a small amount (one drop) of a sample liquid causes the following problem.

That is, a spot-applying operation including dropping a recommended suitable amount of blood on a spot-application region and entirely covering the blood cell separating membrane exposed in the spot-application region with the sample liquid is inconsistent among operators. For example, as shown in FIG. 8, a part of the blood cell separating membrane 122 inside the through hole 130 of the film 120 may not be covered with the sample liquid X10 in some cases.

Such problem occurs not only in blood dropping but also when the above-mentioned standard concentration test solution is dropped as a sample liquid to periodically perform calibration.

When the blood cell separating membrane is not sufficiently covered with a sample liquid (liquid to be dropped such as blood, standard concentration test solution or the like), the amount of a liquid that penetrates to the rear surface of the blood cell separating membrane (analysis target liquid of electrode type sensor) becomes insufficient and problems occur in that the sensor head of the electrode type sensor partly fails to contact the analysis target liquid, and an assumed amount of grape sugar cannot be reacted and the like.

Figure 8:
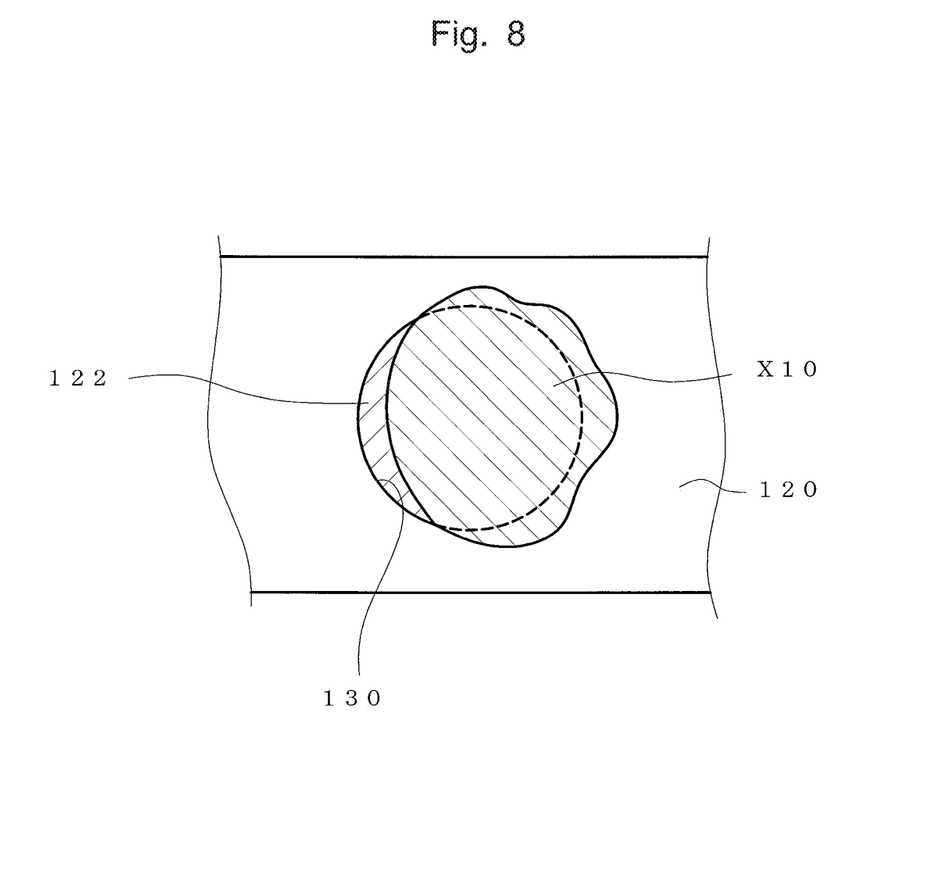
FIG. 8 is an enlarged schematic diagram of a spot-application region of a conventional concentration measuring device, which shows dropped blood and a non-covered region.

After recognizing the problems of dropping failure as mentioned above, when the spot-application region is seen after enlarging as in FIG. 8, it is easy to locate a region in the spot-application region, which is not covered with a sample liquid (non-covered region).

However, in an actual dropping operation, since the diameter of the through hole of the spot-application region is as small as about 4 mm, it is not easy to determine whether a minute non-covered region is present or absent solely by visual observation. In addition, since the dropped blood shows high viscosity, swelling toward the side, a minute non-covered region located in the base part of the dropped blood is sometimes difficult by simply looking into the case opening from above the device.

The problems mentioned above are common to any measuring devices having a constitution for dropping a sample liquid into a small spot-application region (spot-applying), irrespective of the measurement principles such as enzyme electrode method and the like, and the structure of the spot-application region.

An object of the present invention is to suppress the above-mentioned problems, and confer a concentration measuring device with a function enabling easy judgment, by visual observation, of the presence or absence of a non-covered region when a sample liquid is dropped on a spot-application region.

SUMMARY OF THE INVENTION

The present inventors have conducted intensive studies in an attempt to solve the aforementioned problems and found that, when a light having a wavelength absorbable by a coloring matter (color-determining substance) in a sample liquid (blood, test solution for adjustment or the like) to be dropped on a spot-application region is irradiated from the rear surface side of the blood cell separating membrane exposed in the spot-application region, the dropped droplet absorbs the light and remains dark, and only the non-covered region shines brightly to highlight the remarkable difference in brightness between them, thus enabling an easier judgment of the presence of a non-covered region by visual observation, which resulted in the completion of the present invention.

The concentration measuring device of the present invention has the following constitution.

[1] A concentration measuring device having a spot-application region for dropping a sample liquid into, and a configuration capable of measuring the concentration of an object component in the sample liquid dropped on the spot-application region, the concentration measuring device comprising:

a light irradiation device, which is provided on a side below the aforementioned spot-application region, for emitting an irradiation light having a wavelength absorbable by a coloring matter in the dropped sample liquid, wherein the light irradiation device is placed such that the irradiation light passes through the aforementioned spot-application region, thereby the sample liquid dropped on the spot-application region is irradiated with the irradiation light from the side below the spot-application region.

[2] The concentration measuring device of the above-mentioned [1], wherein the above-mentioned spot-application region comprises a through hole provided in a supporting film and a separation membrane for blocking the through hole, the through hole being a hole determining the peripheral shape of the spot-application region, and the separation membrane being a porous thin film allowing penetration of only a liquid component in the sample liquid.

[3] The concentration measuring device of the above-mentioned [1] or [2], which is configured to measure the concentration of an object component in the sample liquid dropped on the above-mentioned spot-application region based on an enzyme electrode method.

[4] The concentration measuring device of any of the above-mentioned [1] to [3], wherein a plurality of sample liquids having different colors are to be dropped, and the above-mentioned light irradiation device is configured to emit plural kinds of lights corresponding to the respective colors and having wavelengths absorbable by respective coloring matters in the sample liquids.

[5] The concentration measuring device of any of the above-mentioned [1] to [3], wherein the sample liquid is blood or a red liquid of processed blood, and the above-mentioned irradiation light is a green light.

[6] The concentration measuring device of any of the above-mentioned [1] to [3], wherein the sample liquid is a standard concentration test solution for calibration of the concentration measuring device for the concentration measurement, the standard concentration test solution has a blue color, and the above-mentioned irradiation light is a red light.

BRIEF DESCRIPTION OF THE DRAWINGS

FIGS. 1A and 1B show the constitution of light irradiation from a side below the spot-application region by a light irradiation device in the concentration measuring device of the present invention and the action effect thereof.

FIGS. 4A-4C show photographs when, in the present invention, a green light was irradiated from the backside of the spot-application region and blood was dropped on the spot-application region.

FIGS. 5A-5C show photographs when, in the present invention, a red light was irradiated from the backside of the spot-application region and a blue standard concentration test solution was dropped on the spot-application region. FIG. 5A shows a spot-application region when the light was irradiated from the backside.

DETAILED DESCRIPTION OF THE INVENTION

In the present invention, a small spot-application region is highlighted against the peripheral film by an unprecedented constitution of illumination of the spot-application region by a backside light. The light irradiation of the spot-application region from the backside clarifies the difference between the region covered by the dropped sample liquid and the non-covered region.

In the present invention, moreover, a particularly important characteristic is that the wavelength of the irradiation light is limited to a wavelength absorbable by a coloring matter in the sample liquid. Due to the limitation on the wavelength, as shown in FIG. 1B, the sample liquid X1 that was dropped on the spot-application region absorbs irradiation light L1 from the backside and remains dark, and only the region not covered by the sample liquid (non-covered region) shines brightly by the irradiation light L1 to highlight the remarkable difference in brightness between the sample liquid X1 and non-covered region, whereby particular action effect apart from a simple backlight is obtained. Utilizing this, the region can be easily distinguished by visual observation, even when the non-covered region is small.

The coloring matter in the present invention is a substance that determines the color of a sample liquid. For example, in blood or a red liquid of processed blood, heme (which binds to oxygen to assume red) in hemoglobin is a substance or material that determines the red color and is a coloring matter in this case. As mentioned below, a pigment to color in blue is added to a standard concentration test solution for calibration of the measuring device. In this case, a substance that determines the blue color of the pigment is the coloring matter. When the pigment is composed solely of a substance that becomes a coloring matter, the pigment substance and the coloring matter are synonymous with each other. The same applies to sample liquids other than blood, various colorants, dyestuff and the like, and a substance that determines the color of the material is the coloring matter.

When plural coloring matters are contained in a sample liquid, one or more suitable coloring matters are selected, and a light having the wavelength absorbed by the coloring matter is determined. That is, the coloring matter and the wavelength of the irradiation light only need to be selected so that the above-mentioned action effect [the sample liquid absorbs irradiation light from the backside and remains dark, and only the non-covered region shines brightly by the irradiation light to highlight the remarkable difference in brightness between the sample liquid and non-covered region, whereby particular action effect apart from a simple backlight] can be obtained, and the irradiation light can be more clearly felt by the operator. While the irradiation light is preferably a monochromatic light or a light having a similar color, a light having a suitable wavelength range according to the coloring matter or a light having plural peak wavelengths may be used as long as the above-mentioned action effect is obtained.

The present invention is explained in detail following the Examples.

Figure 1A:
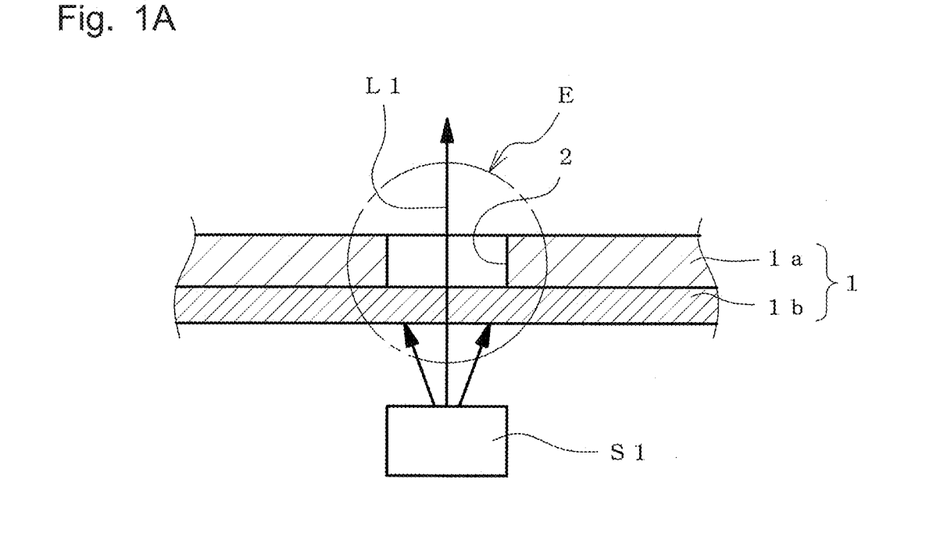
FIG. 1A shows the cross-section of the spot-application region.
Figure 1B:
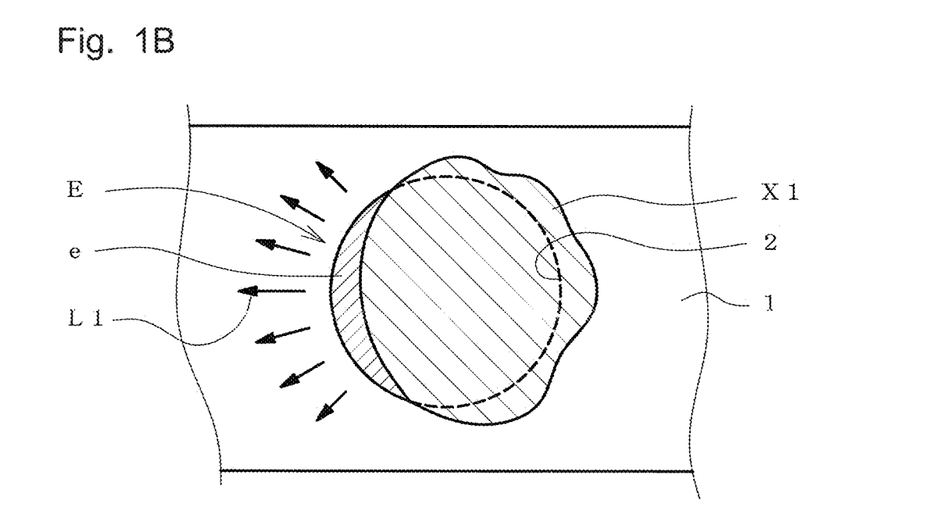
FIG. 1B shows difference in brightness of sample liquid X1 and non-covered region e.

The concentration measuring device of the present invention (hereinafter to be also referred to as the device) is, as shown in FIG. 1A, a concentration measuring device having a spot-application region E for dropping a sample liquid thereon, and is configured to measure the concentration of the object component in the sample liquid (X1 in FIG. 1B) dropped on the spot-application region E.

While the structure of the spot-application region E is not particularly limited, a structure having a through hole provided in a supporting film and a separation membrane for blocking the through hole is preferable, as in the conventional concentration measuring devices. In this case, the through hole is a hole that determines the peripheral shape of the spot-application region, and the separation membrane is a porous thin film allowing penetration of only a liquid component in a sample liquid.

In addition, while the principle of the concentration measurement of the device is not particularly limited, a measurement based on an enzyme electrode method and using an enzyme electrode is a preferable principle, as in the conventional concentration measuring devices.

In the present invention, "measuring the concentration of an object component in the sample liquid" is an operation including not only a measurement of the amount and ratio of the object component contained in a sample liquid but also a simple measurement of the presence or absence of an object component, and whether or not an object component satisfies the standard value.

While a sample liquid to be subjected to the concentration measurement by the device is not particularly limited, blood, a liquid of processed blood, a liquid of blood added with a reagent, a standard concentration test solution to be used for calibration of the device and the like can be recited as representative sample liquids. Especially, measurement of the concentration of a contained component (object component) from one drop of blood (whole blood) is significant for the diagnosis and treatment. In addition, periodical spot-application and calibration of the standard concentration test solution is important for the maintenance and control of the device itself.

When the sample liquid is blood (or a liquid of processed blood or blood added with a reagent), examples of the object components to be measured for the concentration include grape sugar (glucose), uric acid, lactic acid, cholesterol and the like. An electrode type sensor for performing the enzyme electrode method may be selected according to the object component to be measured for the concentration.

The configuration of the electrode type sensor for measuring the blood grape sugar concentration (i.e., blood sugar level) is as described in the section of the BACKGROUND OF THE INVENTION by referring to FIGS. 7A and 7B and the like.

Moreover, the standard concentration test solution for calibration of the device may be appropriately selected according to the above-mentioned object component to be measured for the concentration. When the grape sugar concentration of blood is the object for measurement, an aqueous grape sugar solution having a known concentration (e.g., 150 mg/dL etc.) is used as the standard concentration test solution for calibration. The aqueous grape sugar solution is commercially available by the name of "glucose standard solution" and the like, and generally stained blue with phthalocyanine blue as a pigment for enhancing the distinguishability from blood.

Phthalocyanine blue used as the pigment is the blue coloring matter in the standard concentration test solution in this case.

Figure 2A:
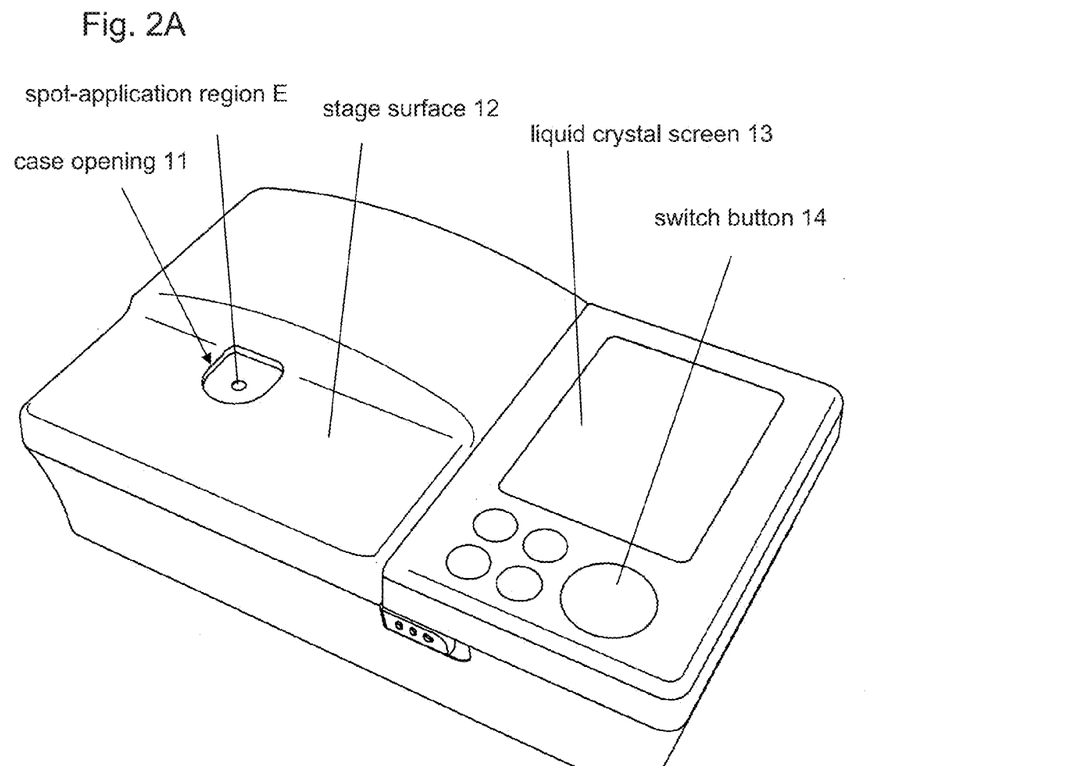
FIGS. 2A and 2B show one embodiment (FIG. 2A) of the appearance of the concentration measuring device of the present invention, and an enlarged view (FIG. 2B) of a case opening formed on the upper surface (stage surface) of the device when seen from the above.

The appearance of the whole device is as shown in FIG. 2A as a preferable embodiment. In the embodiment of FIG. 2A, a spot-application region E is disposed in a case opening 11 provided on a stage surface 12, and a liquid crystal display 13 is provided. Switch button 14 is a button that starts the operation of the device. The appearance of the whole device is not limited thereto, and may be a known design shown in design registration No. 1222931 and the like, or may be more compact or a multifunctional, bulky device installed in a test room.

As shown in FIG. 1A, a preferable embodiment of the spot-application region E is configured with a through hole 2 provided on an opaque supporting film 1a and a separation membrane 1b that blocks the through hole. The detail and more preferable embodiment of the spot-application region are described below.

In the present invention, it is significant that a light irradiation device S1 be provided below the spot-application region E (below of separation membrane 1b in the embodiment of the Figure), as shown in FIG. 1A. The light irradiation device is provided such that the irradiation light L1 passes through the aforementioned spot-application region E, whereby, as shown in FIG. 1A, sample liquid X1 dropped on the spot-application region E can be illuminated from the side below, through the spot-application region E. The light irradiation device S1 is not necessary fixed below the spot-application region E, but only needs to be positioned below the spot-application region E at least at the time of spot-application and be irradiated.

In a preferable embodiment of the spot-application region E, the irradiation light L1 emitted from the light irradiation device S1 penetrates the separation membrane 1b and passes through the through hole 2, as shown in FIG. 1A.

A more important point here is that the irradiation light L1 is a light having a wavelength absorbable by the coloring matter in the sample liquid X1. With this characteristic, the irradiation light L1 not only functions as the backlight of the spot-application region E but also is, as shown in FIG. 1B, absorbed by the dropped sample liquid X1 to allow the sample liquid X1 to remain dark, and brightly illuminates only the non-covered region e to highlight the remarkable difference in brightness between the sample liquid X1 and the non-covered region e, which in turn enables easy discovery of the non-covered region e by visual observation even when it is small.

FIG. 1A shows a preferable structure of the spot-application region E, wherein a supporting film 1a on the upper layer side (operator side) and a separation membrane 1b on the lower layer side (inside of device side) are laminated on each other, like the conventional example shown in FIGS. 7A and 7B, the separation membrane 1b blocking a through hole 2 of the supporting film 1a. Film 1 is band-like, which is a preferable embodiment. The width and full-length of the film 1 can be determined as appropriate according to the size of the device and by reference to conventional techniques. The spot-application region E is formed in the belt-shaped film 1 at a given distance, and an embodiment wherein a new spot-application region is made to sequentially appear in the center of the case opening for each measurement is preferable.

In a preferable embodiment, it is constituted that a necessary amount of the film 1 is intermittently fed from a delivery roll (not shown) to a winding roll (not shown), and film 1 as a whole including the delivery roll and the winding roll is provided as a replaceable cartridge. In a preferable embodiment, a driving source for driving the cartridge and feeding the film 1 is set on the device side.

While film 1 may be largely exposed on the outer surface of the device, in a preferable embodiment, the film is disposed beneath a topical case opening (through hole) 11 formed in the upper surface of the case in the device (stage surface 12 in FIG. 2A), and fed at a suitable timing to position a new spot-application region E right beneath the case opening 11 for every measurement, like the conventional example shown in FIGS. 7A and 7B.

While the shape and size of the case opening 11 are not particularly limited, it is a circular shape with a diameter of about 25 mm-35 mm in the conventional products shown in design registration No. 1222931 and the like. In the Example product of the present invention shown in FIG. 2A, it is a combined form of a semicircle (diameter about 25 mm-35 mm) and a rectangle, which is widely expanded to facilitate the operation of spot-application.

As mentioned above, a preferable structure of film 1 is band-like, and a layered structure of the supporting film 1a and the separation membrane 1b. The supporting film 1a has through holes 2 to be the opening of the spot-application region at a given distance in the longitudinal direction (film feeding direction), and the upper surface of the separation membrane 1b is exposed on the bottom of the through hole.

In a preferable structure, the spot-application region E is configured by the through hole 2 and the separation membrane 1b as the internal bottom. Depending on the structure of the film 1, the separation membrane 1b does not need to be present as the internal bottom of the through hole 2 but only needs to be provided to block the through hole.

The material of the supporting film 1a is not particularly limited, and may be a material of a supporting film used in conventionally known concentration measuring devices. Preferable examples of such material include PE (polyethylene), PET (polyethylene terephthalate), PVC (polyvinyl chloride), PC (polycarbonate) and the like, since they have mechanical strength as a support standing the delivery of a film, do not change form even when water is contained, do not stretch even when pulled, do not show change of material quality even when an adhesive attaches, and the like.

While the thickness of the supporting film 1a is not particularly limited and may be appropriately determined according to the mechanical strength of the material, it is preferably about 30-40 μm.

In the present invention, the supporting film 1a is preferably opaque. This is because the irradiation light L1 that was emitted from the side below the film 1 and passed through the separation membrane highlights the brightness of the spot-application region E alone when viewed from above the spot-application region E, as shown in FIG. 1B.

Being opaque here means not only complete prevention of the penetration of the irradiation light L1 but also non-transparency of the supporting film surface by visual observation. The supporting film 1a may permit penetration of the irradiation light L1 as long as the effect of the present invention [only the spot-application region E shines brightly by irradiation light L1 emitted from the side below] is obtained. The supporting film preferably has a penetrate rate of not more than about 80%, more preferably not more than about 70%, of irradiation light relative to the film thickness direction, since the difference in brightness between the spot-application region E and the periphery thereof is clarified.

When the color of the sample liquid is highly dark such as red of blood, blue of the standard concentration test solution and the like, the color of the supporting film 1a is preferably opaque and bright such as white, milky white and the like, since such color facilitates visual distinguishing of the external range of the dropped sample liquid.

The supporting film 1a may have a laminate structure consisting of a plurality of layers, including a layer for ensuring the property required of the supporting film such as mechanical strength and the like and an opaque layer for blocking the irradiation light L1.

While the shape of the spot-application region E, that is, the shape and size of the through hole 2, when the supporting film 1a is viewed from above is not particularly limited, a circular shape is preferable since a sample liquid is dropped thereon. The diameter of the spot-application region E in this case is preferably 3 mm-5 mm, and 4 mm in the examples shown in FIG. 3A-FIG. 5C.

The separation membrane 1b may be a filter membrane configured to permit penetration of only liquid (blood plasma) to be the analysis object from the dropped sample liquid. In addition, the separation membrane 1b preferably permits penetration of a larger amount of irradiation light than the supporting film, to afford the effect of the present invention, [only the spot-application region E shines brightly by irradiation light L1 emitted from the side below]. When the sample liquid is blood (or a liquid of processed blood or blood added with a reagent), a conventionally known blood cell separating membrane may be used as a separation membrane.

The blood cell separating membrane is made from a material such as PET, PVC, PE, PC and the like, has a thickness of about 5-10 μm, and is a porous filter membrane having many minute through holes with a diameter of about 0.1-0.5 μm dispersed so that only blood plasma can penetrate the membrane. The blood cell separating membrane permits sufficient penetration of the irradiation light, as shown in FIG. 3B, by the material, thickness and porosity thereof.

A method of forming film 1 having a laminate of a supporting film 1a and a separation membrane 1b, and a through hole 2 may be a conventional technique. For example, a method including interposing an adhesive layer such as a double-faced adhesive tape and the like between a supporting film and a separation membrane and laminating them and the like can be mentioned. The through hole 2 can be formed, for example, by laminating an adhesive layer on a supporting film 1a, forming a through hole 2, and then laminating a separation membrane 1b.

The irradiation light may be any light as long as it has a wavelength absorbable by the coloring matter in the dropped sample liquid. To be more specific, a light having a complementary color (opposite color) to the color of a sample liquid to be dropped, or a light having a color phase close to the complementary color (color phase near the complementary color in hue circle) is preferable. Irradiation of a light with a color similar to that of the coloring matter in a sample liquid or a light with a broad wavelength (white color light and the like), as the irradiation light, is not preferable, since the light is not absorbed by the dropped sample liquid droplet, and the sample liquid droplet also becomes bright to reduce the difference in brightness from the non-covered region. The irradiation light preferably has a noticeable color for the operators.

As a specific example, when the sample liquid to be dropped is blood or a red liquid of blood processed by dilution or addition of a reagent, the irradiation light is preferably a green light (wavelength about 500 nm-570 nm)-blue light (wavelength about 450 nm-500 nm). The wavelength range of the aforementioned green light includes a light in a color phase recognized as yellowish green. A green light is absorbed well by the red coloring matter (hem which binds to oxygen to assume red) of hemoglobin in the blood and, as shown in FIG. 1B, the action effect of the present invention is remarkably obtained, since the sample liquid X1 that was spot-applied remains dark, and only the non-covered region e shines brightly by the green irradiation light L1 to highlight the difference in brightness between the sample liquid X1 and non-covered region e for the operator. Use of a blue light for visual observation is not preferable since it may damage the retina, and a green light is preferable also from such aspects.

When a sample liquid to be dropped is a standard concentration test solution (blue), the irradiation light is preferably a yellow light (wavelength about 570 nm-600 nm)-red light (wavelength about 600 nm-750 nm). Of these, a red light is preferable as a light remarkably affording the aforementioned action effect of the present invention since, although it is not theoretically complementary to blue, it is well absorbed by the coloring matter in the standard concentration test solution and is highly noticeable to the operator even with a small amount of leakage.

While the light source of a light irradiation device emitting the aforementioned irradiation light is not particularly limited, a light emitting diode (LED) is preferable since it is compact and can comparatively freely select an element that emits a light having a wavelength range suitable for the above-mentioned object (green light of InGaN-based semiconductor, yellowish green light-yellow light of GaP-based semiconductor, yellow light-red light of AlGaInP-based semiconductor and the like) from commercially available products.

Among LEDs, a surface-mounted (chip type) LED having an external shape with one side being about 1 mm-2 mm is more preferable, since a plurality of such LED can be mounted on a substrate right beneath the spot-application region, and can be accommodated in the range of the spot-application region. Where necessary, a composite element configured to emit two or more colors with one chip by switching the lights may be used.

In the constitution of FIG. 1A, a masking plate, which have a through hole having the same diameter as that of the spot-application region, a lens, a wave guide and the like, may be formed between the separation membrane 1b and the light irradiation device S1, to ensure irradiation of irradiation light L1 only through the through hole in the spot-application region.

The device may be constituted such that an irradiation light can be emitted onto at least a sample liquid (sample such as blood and the like) to be the target of concentration measurement. When a plurality of sample liquids having different colors, such as standard concentration test solution for calibration and the like, are the targets of concentration measurement, the above-mentioned light irradiation device is configured to emit plural kinds of lights corresponding to the respective colors and having wavelengths absorbable by respective coloring matters in the sample liquids.

For example, a green LED chip for blood (red) and a red LED for a standard concentration test solution (blue) for calibration may be mounted on a substrate right beneath the spot-application region, and a blood measurement mode and a calibration mode are converted by a switch on an operation panel, thereby irradiating the green light on the blood and the red light on the standard concentration test solution.

The irradiation of light from the backside of the spot-application region may be started when the device is turned on, like a power source lamp, or the light may be flashed for a given period.

Figure 3A:
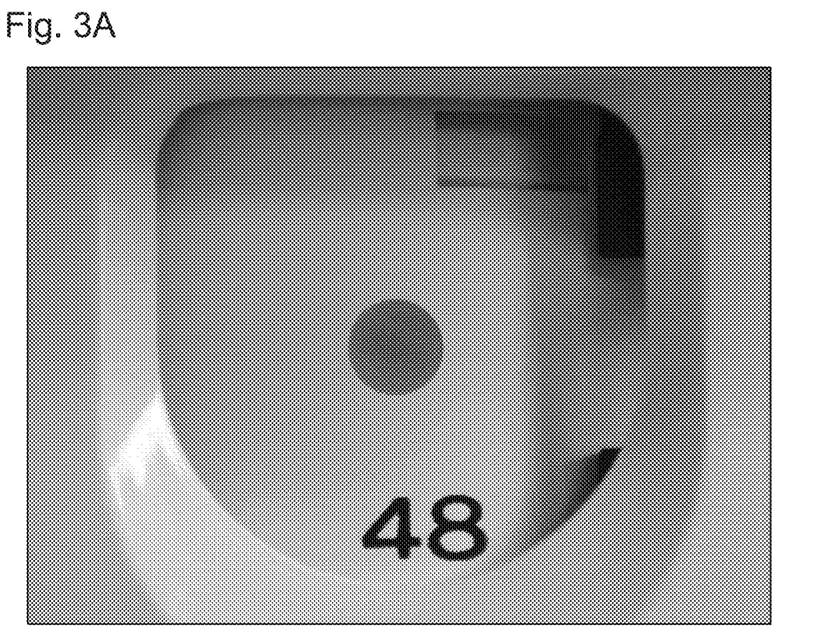
FIGS. 3A and 3B shows photographs of, in the present invention, the spot-application region (FIG. 3A) without light irradiation from the backside, and spot-application region (FIG. 3B) with irradiation of a green light from the backside.
Figure 3B:
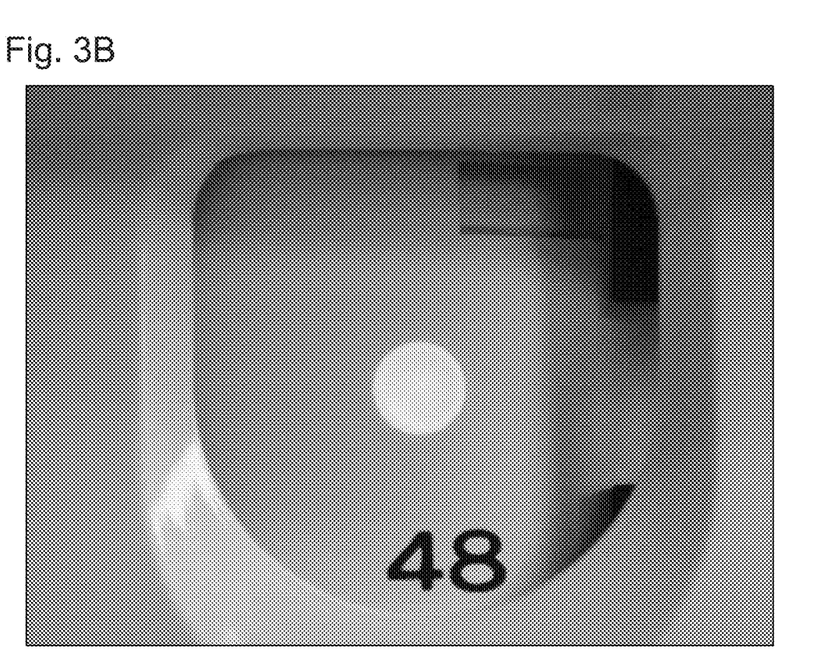
Figure 4A:
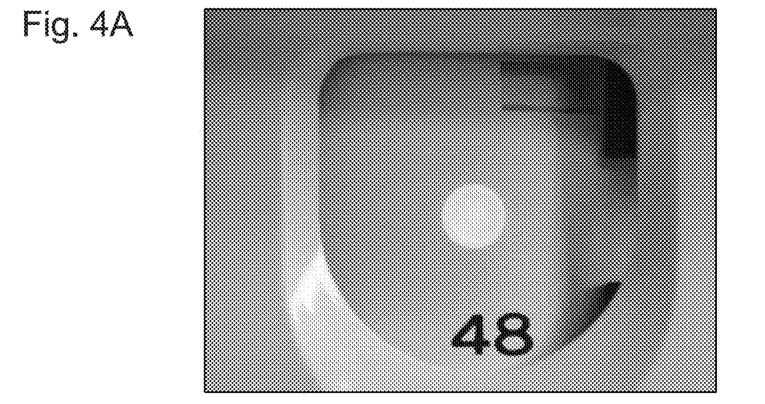
FIG. 4A is the same photograph as FIG. 3B, except that the light was irradiated from the backside of the spot-application region.
Figure 4B:
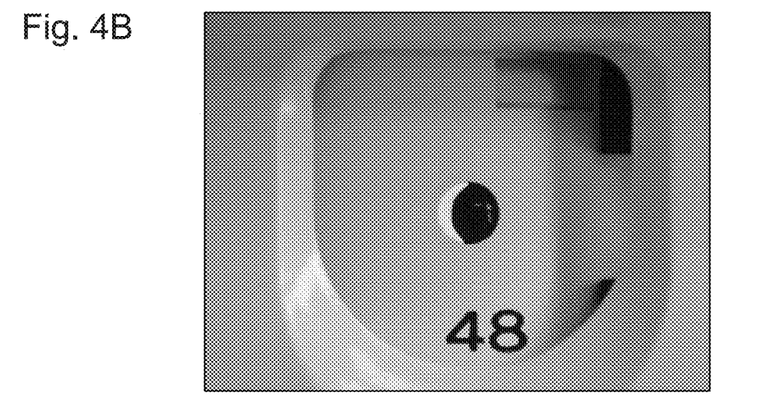
FIG. 4B shows an intentionally formed non-covered region by dropping blood on the spot-application region of FIG. 4A.
Figure 4C:
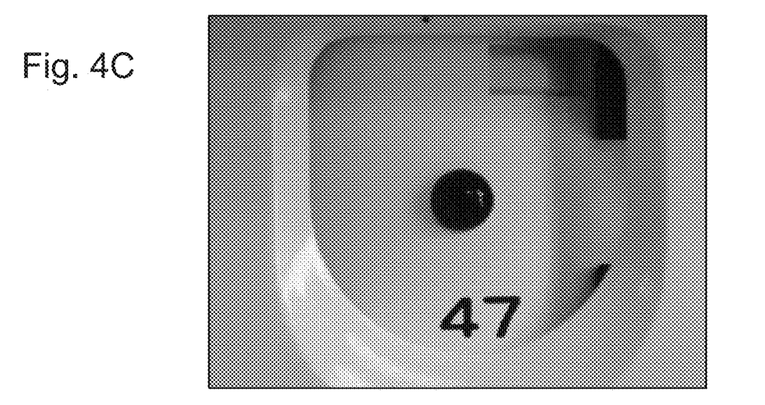
FIG. 4C shows an entirely-covered spot-application region by dropping sufficient blood on the spot-application region.
Figure 5A:
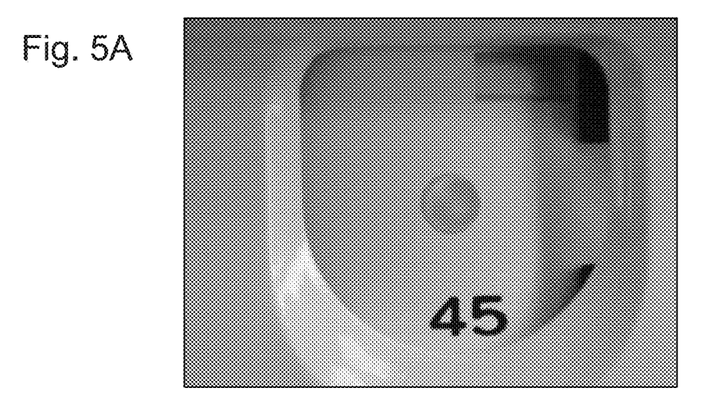
Figure 5B:
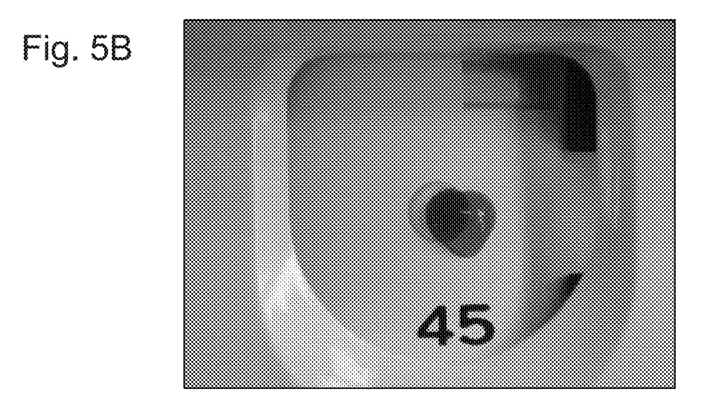
FIG. 5B shows an intentionally formed non-covered region by dropping a blue standard concentration test solution on the spot-application region of FIG. 5A.
Figure 5C:
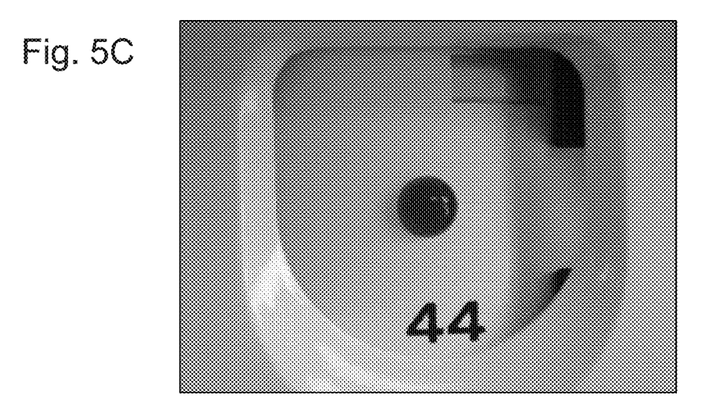
FIG. 5C shows an entirely-covered spot-application region by dropping sufficient blood on the spot-application region.

FIGS. 3-5 shows an experiment including actually producing the concentration measuring device of the present invention, and dropping (spot-applying) a sample liquid while irradiating a light from the backside of the spot-application region to confirm distinguishability of a non-covered region.

Figure 2B:
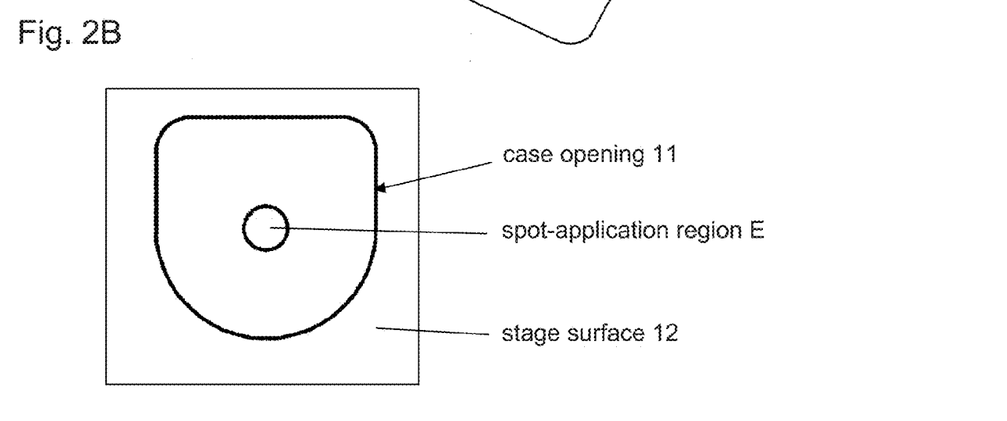

In this experiment, the shape of the case opening is a combination of a semicircular shape (diameter 30 mm) and a quadrate, as in FIG. 2B, and the spot-application region is a circular shape having a diameter of 4 mm. The numbers appearing in the case opening in respective FIGS. 3-5 are the numbers of the spot-application regions printed on the film surface.

FIG. 3A shows the spot-application region without light irradiation from the backside (similar to conventional products), and FIG. 3B shows the spot-application region E with irradiation of a green light from the backside. In this embodiment, the green irradiation light is a light having a center wavelength of 570 nm from a GaP-based LED.

FIGS. 4A-4C show photographs of an experiment in which a green light was irradiated from the backside of the spot-application region and blood was dropped. FIG. 4A is the same photograph as FIG. 3B, except that a green light was irradiated from the backside of the spot-application region. FIG. 4B is a photograph of a non-covered region intentionally formed by dropping blood on the spot-application region in the irradiation state of FIG. 4A. FIG. 4C is a photograph of a spot-application region entirely covered by dropping sufficient blood on the spot-application region.

By comparison of FIG. 4B and FIG. 4C, the dropped blood remained dark even when a green light was irradiated from the side below, but a non-covered region, when it is present, alone shines brightly to facilitate recognition.

FIGS. 5A-5C show photographs of an experiment in which a red light was irradiated from the backside of the spot-application region and a blue standard concentration test solution was dropped thereon. In this embodiment, the red irradiation light is a light having a central wavelength of 620 nm from an AlGaAs-based LED.

FIG. 5A shows a spot-application region when a red light was irradiated from the backside of the spot-application region. FIG. 5B is a photograph of a non-covered region intentionally formed by dropping a blue standard concentration test solution on the spot-application region in the irradiation state of FIG. 5A. FIG. 5C is a photograph of a spot-application region entirely covered by dropping sufficient standard concentration test solution on the spot-application region.

By comparison of FIG. 5B and FIG. 5C, the dropped blue standard concentration test solution remained dark even when a red light was irradiated from the side below, but a non-covered region, when it is present as in FIG. 5B, alone shines brightly in red to facilitate recognition of the operator.

Figure 6:
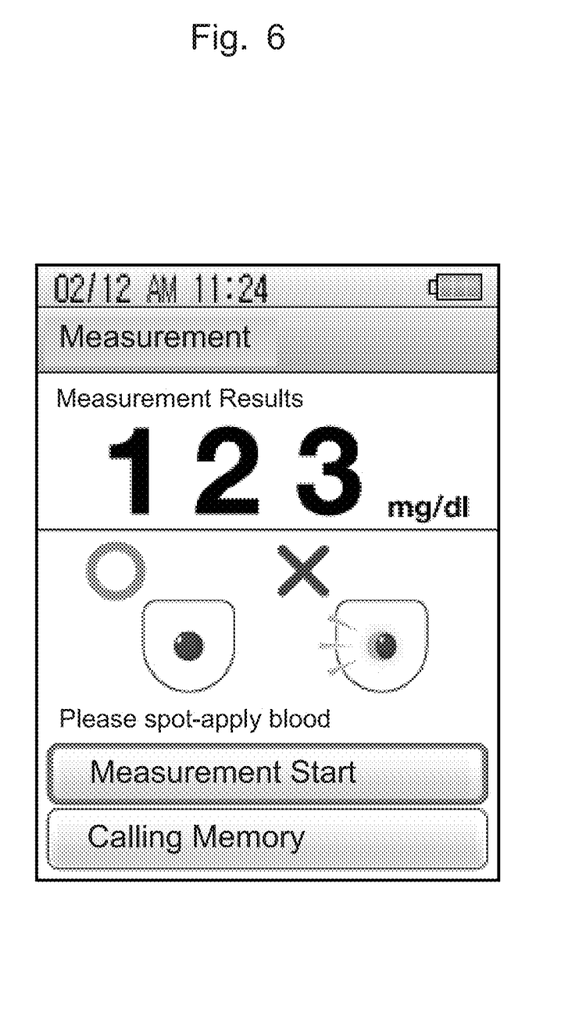
FIG. 6 shows an example of an indication on a display screen in the present invention.

The display screen (liquid crystal screen) of the device may indicate, as shown in FIG. 6, a sufficient drop state wherein the whole spot-application region is covered with a sample liquid, and an insufficient drop state wherein the non-covered region is present, call attention of the user and raise consciousness for prevention of dropping failure.

The film feeding mechanism in the device, a detailed constitution of an electrode type sensor for concentration measurement based on an enzyme electrode method, the mechanism for upward/downward movement of the sensor, and the constitution of a control part for the film feeding mechanism and the electrode type sensor, calculating the concentration from the obtained measurement signals and outputting the results may be the techniques of the details of the conventional concentration measuring devices.

The concentration measuring device of the present invention has enabled easy visual observation of the presence or absence of a non-covered region when a sample liquid is dropped on a spot-application region.

This application is based on patent application No. 2013-146959 filed in Japan, the contents of which are incorporated by reference in full herein.

The invention claimed is:

1. A concentration measuring device having a spot-application region for dropping a sample liquid into, and a configuration capable of measuring the concentration of an object component in the sample liquid dropped on the spot-application region,
   the concentration measuring device is configured:
      to move the spot-application region with the dropped sample liquid to a position different from the position at which the sample liquid was dropped, and
      to measure the concentration of an object component in the sample liquid dropped on the spot-application region based on an enzyme electrode method, by an electrode type sensor provided on a side below the moved spot-application region,
   the concentration measuring device comprising:
   a light irradiation device, which is provided on a side below the spot-application region at the position at which the sample liquid is dropped, for emitting visible light having a wavelength absorbable by a coloring matter in the dropped sample liquid,
   wherein the light irradiation device is placed such that the visible light passes through the spot-application region, thereby the spot-application region and the sample liquid dropped on the spot-application region are irradiated with the visible light from the side below the spot-application region.

2. The concentration measuring device according to claim 1, wherein the spot-application region comprises a through hole provided in a supporting film and a separation membrane for blocking the through hole, the through hole being a hole determining the peripheral shape of the spot-application region, and the separation membrane being a porous thin film allowing penetration of only a liquid component in the sample liquid.

3. The concentration measuring device according to claim 1, wherein a plurality of sample liquids having different colors are to be dropped, and the light irradiation device is configured to emit plural kinds of lights corresponding to the respective colors and having wavelengths absorbable by respective coloring matters in the sample liquids.

4. The concentration measuring device according to claim 1, wherein the sample liquid is blood or a red liquid of processed blood, and the visible light is a green light.

5. The concentration measuring device according to claim 1, wherein the sample liquid is a standard concentration test solution for calibration of the concentration measuring device for the concentration measurement, the standard concentration test solution has a blue color, and the visible light is a red light.

* * * * *